(12) United States Patent
Eggert et al.

(10) Patent No.: US 9,610,406 B2
(45) Date of Patent: Apr. 4, 2017

(54) DISPENSE INTERFACE FOR AN EJECTION DEVICE

(71) Applicant: SANOFI-AVENTIS DEUTSCHLAND GMBH, Frankfurt am Main (DE)

(72) Inventors: Ilona Eggert, Frankfurt am Main (DE); Frederic Laugere, Bedfordshire (GB); Cristian Popa, Norfolk (GB); Ben Impey, Cambridgeshire (GB); Andrew Macleod, Cambridgeshire (GB)

(73) Assignee: SONOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/412,729

(22) PCT Filed: Jul. 10, 2013

(86) PCT No.: PCT/EP2013/064631
§ 371 (c)(1),
(2) Date: Jan. 5, 2015

(87) PCT Pub. No.: WO2014/009443
PCT Pub. Date: Jan. 16, 2014

(65) Prior Publication Data
US 2015/0157797 A1    Jun. 11, 2015

(30) Foreign Application Priority Data
Jul. 11, 2012 (EP) .................................... 12175975

(51) Int. Cl.
*A61M 5/19* (2006.01)
*A61M 5/24* (2006.01)
(Continued)

(52) U.S. Cl.
CPC ............ *A61M 5/19* (2013.01); *A61M 5/2448* (2013.01); *A61M 5/2455* (2013.01);
(Continued)

(58) Field of Classification Search
CPC .... A61M 5/19; A61M 5/2448; A61M 5/2455; A61M 5/31–5/32;
(Continued)

(56) References Cited

U.S. PATENT DOCUMENTS

| | | | | | |
|---|---|---|---|---|---|
| 5,314,412 | A | * | 5/1994 | Rex | .......................... A61M 5/19 222/137 |
| 5,443,453 | A | * | 8/1995 | Walker | ................. F16K 11/0853 137/625.41 |

(Continued)

FOREIGN PATENT DOCUMENTS

| | | |
|---|---|---|
| WO | 94/22507 | 10/1994 |
| WO | 2007/137436 | 12/2007 |
| WO | 2012/072559 | 6/2012 |

OTHER PUBLICATIONS

International Search Report for Int. App. No. PCT/EP2013/064631, completed Sep. 20, 2013.
European Examination Report for EP App. No. 13735039.3, dated Mar. 17, 2016.

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

The invention inter alia relates to a dispense interface for an ejection device. The dispense interface comprises at least two inlets, at least one outlet, a body part, and a fluid channel arrangement within the body part configured to provide fluid communication between the at least two inlets and the at least one outlet; wherein each of the at least two inlets is formed from a tubelike fluid element; wherein each of the tubelike fluid elements is molded into the body part; and wherein each of the tubelike fluid elements provides at least a part of the fluid channel arrangement within said body part.

12 Claims, 15 Drawing Sheets

(51) Int. Cl.
    *A61M 5/32*     (2006.01)
    *A61M 5/34*     (2006.01)
    *A61M 39/22*    (2006.01)
    *A61M 5/31*     (2006.01)

(52) U.S. Cl.
    CPC ........ *A61M 5/3294* (2013.01); *A61M 5/3295* (2013.01); *A61M 5/343* (2013.01); *A61M 39/223* (2013.01); *A61M 2005/3128* (2013.01); *A61M 2205/12* (2013.01); *A61M 2205/121* (2013.01); *A61M 2207/00* (2013.01)

(58) Field of Classification Search
    CPC ........ A61M 2005/3128; A61M 205/12; A61M 2205/121; A61M 2207/00; A61M 3/005; A61M 5/16827; A61J 1/20; F16K 3/04; F16K 3/06
    See application file for complete search history.

(56) References Cited

U.S. PATENT DOCUMENTS

| | | | | |
|---|---|---|---|---|
| 5,478,323 | A * | 12/1995 | Westwood | A61M 5/19 604/191 |
| 5,505,721 | A * | 4/1996 | Leach | A61B 5/1427 604/257 |
| 5,542,934 | A * | 8/1996 | Silver | A61M 5/19 604/191 |
| 6,328,229 | B1 * | 12/2001 | Duronio | B01F 5/0057 222/145.5 |
| 6,620,138 | B1 * | 9/2003 | Marrgi | A61M 5/1408 604/110 |
| 8,105,281 | B2 * | 1/2012 | Edwards | A61M 5/19 141/2 |
| 2008/0214993 | A1 * | 9/2008 | Haarala | A61M 39/223 604/44 |

* cited by examiner

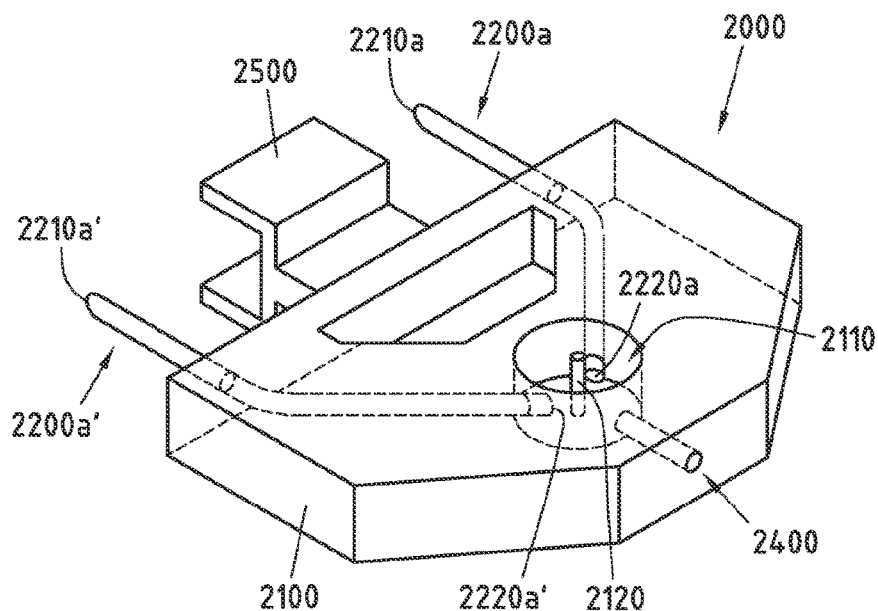
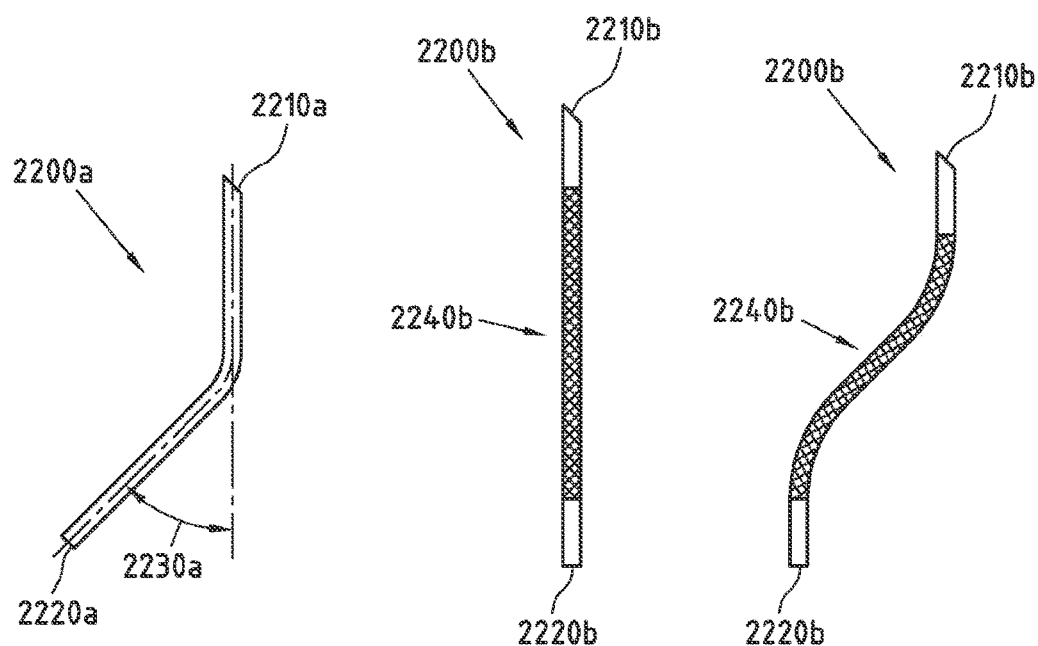
Fig.12a    Fig.12b    Fig.12c    Fig.12d

DISPENSE INTERFACE FOR AN EJECTION DEVICE

CROSS REFERENCE TO RELATED APPLICATIONS

The present application is a U.S. National Phase Application pursuant to 35 U.S.C. §371 of International Application No. PCT/EP2013/064631 filed Jul. 10, 2013, which claims priority to European Patent Application No. 12175975.7 filed Jul. 11, 2012. The entire disclosure contents of these applications are herewith incorporated by reference into the present application.

TECHNICAL FIELD

The present patent application relates to an ejection device, for example a medical device, for delivering at least two liquids, such as liquid drug agents, from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The dispense interfaces in the state of the art, however, are often of complex design. In order to provide the manifold to guide the medicaments from two different reservoirs to a single outlet, complex and/or multiple small parts need to be produced and assembled. The complex part structures and the corresponding complicated assembly steps may cause the dispense interface to be difficult and expensive to manufacture.

Additionally, the dispense interface is regularly kept at the drug delivery device for a longer period of time. This means that only the dose dispenser in form of a double ended needle, for instance, is exchanged for every (or nearly every) injection procedure. The dispense interface, however, remains at the drug delivery device. An exchange of the dispense interface itself is regularly only necessary, when the reservoirs of the drug delivery device need to be exchanged.

This causes requirements for the material and design of the dispense interface to be fulfilled. Since the drug agents from the first and/or the second reservoir remain inside the dispense interface after a dispense procedure, a compatibility of the dispense interface being in contact with the drug agents needs be to provided. No harmful substances must diffuse into the drug agents, since these would then be delivered to the patient with the next delivery procedure. Hence a biocompatibility is required, which guarantees that either no or negligible amounts of substances can diffuse into drug agents or are set free into the liquid.

Furthermore, if the dispense interface remains attached to the drug delivery device the different drug agents also start to diffuse into each other over time. A cross-contamination of the drug agents from one reservoir into the other reservoir needs to be prevented for the above mentioned reasons of stability, compromised therapeutic performance and toxicology, for example.

In light of the aforementioned, the invention inter-alia faces the technical problem of providing a simple dispense interface for an ejection device that is easy to manufacture.

According to a first aspect of the invention, a dispense interface for a an ejection device comprises at least two inlets, at least one outlet, a body part, and a fluid channel arrangement within the body part configured to provide fluid communication between the at least two inlets and the at least one outlet; wherein each of the at least two inlets is formed from a tubelike fluid element; wherein each of the tubelike fluid elements is molded into the body part; and wherein each of the tubelike fluid elements provides at least a part of the fluid channel arrangement within said body part.

The ejection device may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day. In particular, the ejection device may be a medical device configured to deliver (e.g. eject) at least two drug agents from separate reservoirs.

Alternatively, the ejection device may for instance be configured to deliver (e.g. eject) a two-component adhesive from separate fluid reservoirs comprising a first component of the two-component adhesive (e.g. a binder) and a second component of the two-component adhesive (e.g. a hardener), respectively.

The dispense interface may be a disposable part attachable to the ejection device (e.g. the medical device). In particular, the dispense interface may be a single-use part attachable to the ejection device. Each of the at least two inlets of the dispense interface may be configured to reside in fluid communication with one of at least two separate fluid reservoirs of the ejection device when the dispense interface is attached to the ejection device.

The ejection device and/or the dispense interface may preferably be portable (e.g. handheld) devices.

The fluid channel arrangement may provide a fluid connection between each of the at least two inlets of the dispense interface and the at least one outlet of the dispense interface. Also, the fluid channel arrangement may provide a fluid connection between the at least two inlets of the dispense interface. For instance, the fluid channel arrangement is at least partially Y-like, T-like or Z-like shaped.

The at least one outlet of the dispense interface may serve as a common outlet for separate fluid reservoirs of the ejection device. As described above, each of these separate fluid reservoirs may reside in fluid communication with one of the at least two inlets of the dispense interface when the dispense interface is attached to the ejection device.

The fluid channel arrangement within the body part may comprise one or more connected fluid channels, which inter alia are at least partially provided by the tubelike fluid elements. The diameter of the fluid channels may be between 0.01 mm and 10 mm. In particular, the diameter of the fluid channels may be between 0.1 mm and 1 mm, for instance about 0.3 mm. The ratio between the length of the fluid channel arrangement and the diameter of the fluid channels (length:diameter ratio) may be substantially large, for instance between 10:1 and 1000:1. In particular, the length:diameter ratio may be between 20:1 and 100:1, for instance about 33:1 or 66:1. The length of the fluid channel arrangement may preferably describe the longest fluid path of the fluid channel arrangement. Since the tubelike fluid elements provide at least a part of the fluid channel arrangement, the tubelike fluid elements may comprise the same dimensions as set out above.

Integrally formed parts having a fluid channel arrangement with a substantially large ratio between the length of the fluid channel arrangement and the diameter of the fluid channels (length:diameter ratio) cannot be simply manufactured, for instance by molding such as injection molding e.g. in gas molding process. This is inter-alia due to the fact that the fluid channel arrangement is difficult to access. Complex tooling is necessary to manufacture such parts.

By providing a dispense interface, wherein each of the tubelike fluid elements is molded into the body part, a fluid channel arrangement can be provided within a dispense interface having a large ratio between the length of the fluid channel arrangement and the diameter of the fluid channels. At the same time the dispense interface may be provided in an easy way without any complex tooling.

Molding the tubelike fluid elements into the body part particularly means that the process of over-molding is utilized. The tubelike fluid elements and the body part thus form an integral part. The tubelike fluid elements may be positioned in a mold or shell, for example. The body part may then be molded which fixes each of the tubelike fluid elements in a predetermined position.

The tubelike fluid elements may be molded partially or completely into the body part. Preferably, at least a first end of each of the tubelike fluid elements protrudes from the body part. Each end may be used to establish a releasable fluid connection with the ejection device, for instance with a first and a second reservoir of the ejection device, respectively. A second end of each of the tubelike fluid element may also protrude from the body part, for example into an ullage, which may be formed in the body part during the molding process. Each of the tubelike fluid elements preferably has two ends. However, more than two, e.g. three or four, tubelike fluid elements may be used providing a more complex fluid channel arrangement. Alternatively or additionally, more complex tubelike fluid elements, for example with more than two ends, may be used, as well.

The molding process of the body part, during which each of the tubelike fluid elements is molded into the body part, may be an injection molding process. For instance, the body part is formed in a single step by injection molding by use of an open-and-shut tool.

For instance, use of an open-and-shut tool reduces the need for fragile core pins. This also allows for relatively complex and tight tolerance geometry without complex tooling. The molding of key assembly snap features on the same component, such as an outer protrusion on the body part, may also help reduce tolerance stack-ups and also tends to allow for smaller fluid grooves (e.g. needle wells) and therefore smaller ullage.

Alternative also the in gas pressure molding process forms a good surface inside the ullage area of the body part.

For instance, the body part may be a plastic part from a thermoplastic or a thermosetting material. Polymer materials may be used in injection molding of the body part. Polymer materials are typically biocompatible. For instance, COP (cyclo-olefin polymer) materials may be used in injection molding of the body part. COP materials have a high biocompatibility. For instance, COP materials have little to no extractables and most COP materially can undergo sterilization by gamma radiation, steam and/or ethylene oxide. Other materials such as PP (poly-propylene) or HDPE (high density poly-ethylene) or other less expensive materials may be used, too. Especially, the body part of a single use dispense interface may be made from such a material, as the contact time with the medicament is rather short (only the time from priming the device until the injection is completed).

Biocompatibility may be increased by providing tubelike fluid elements made of steel, in particular stainless steel, e.g. EN steel no. 1.4401 or 1.4405, or alternative titan For instance, a fluid being guided by one of the tubelike fluid elements does not get in contact with the body part as long as it is guided by the tubelike fluid element. This may increase freedom when choosing a material for the molding process of the body part. In addition to reach a very clean and accurate inner surface of the tube, the tubes can be electro-polished.

By providing a dispense interface wherein each of the tubelike fluid elements provides at least a part of the fluid channel arrangement, the tubelike fluid elements may reduce or eliminate the contact area and/or contact time of the liquid guided through the dispense interface with the material of the body part.

The dispense interface of the first aspect of the invention thus allows a simple manufacturing of the dispense interface, in particular in a single manufacturing step. Furthermore, the count and complexity of the assembly parts of the dispense interface is reduced. The invention is therefore inter alia advantageous to allow a simple manufacturing and/or assembly of a dispense interface. Also, it allows a cost-effective manufacturing assembly of a disposable dispense interface (e.g. a single use dispense interface). Particularly, potential problems of material compatibility, absorption and cross contamination between the fluids (e.g. drugs) and the polymer material may be overcome by providing a dispense interface wherein each of the tubelike fluid elements provides at least a part of the fluid channel arrangement and/or—for a single use dispense interface—by a short contact time. In this way, also a reduction in the cost of goods can be achieved.

According to an exemplary embodiment of the dispense interface of the first aspect of the invention, each of the tubelike fluid elements is configured to establish a releasable fluid connection with a corresponding fluid connector of a fluid reservoir of the ejection device when the dispense interface is attached to the ejection device.

Each of the tubelike fluid elements may be designed as a piercing needle, for example. The corresponding fluid connector may be a piercable septum in that case. Alternatively or additionally, there may also be provided (male/female) Luer-connectors or snap locks on the body part, for example.

According to an exemplary embodiment of the dispense interface of the first aspect of the invention, each of the tubelike fluid elements is at least partially curved. Each of the tubelike fluid elements may exhibit one or more sections of constant curvature or of varying curvature. The tubelike fluid elements may also show an S-shaped double curvature. Each of the tubelike fluid elements may comprise one or more sections with substantially no curvature (a substantially linear section). The sections with no curvature are preferably at the end or the ends of the tubelike fluid elements, while the curved sections are in between. An application-specific shape of the tubelike fluid elements and thus of the fluid channel arrangement can be provided. In case sections, preferably the ends, of the tubelike fluid elements protrude from the body part, preferably, the sections protruding from the body part are substantially linear sections.

According to an exemplary embodiment of the dispense interface of the first aspect of the invention, each of the tubelike fluid elements is a needle or a hypo-tube. A hypo-tube is a tube with application-specific properties, for example mechanical or chemical properties, used in the medical area. A hypo-tube may be manufactured from stainless steel. In combination with internal and/or external coatings the properties of the hypo-tube may be influenced. For instance, the hypo-tube may be laser cut, for example helically, increasing the mechanical flexibility of the hypo-tube. Additionally or alternatively, a polymer sheath may be provided on the outside and/or inside of the hypo-tube to ensure fluid tightness. In case each of the tubelike fluid elements is a needle, the needle may also be manufactured from steel, in particular stainless steel, providing a good biocompatibility. The hypo-tube or the needle may be molded into the body part, such that the end of the hypo-tube or the needle tip protrudes from the body part, in particular substantially perpendicularly.

According to an exemplary embodiment of the dispense interface of the first aspect of the invention, the at least one outlet is formed from a fluid connector, wherein the fluid channel arrangement empties into the fluid connector, and wherein the fluid connector is configured to establish a fluid connection with a corresponding fluid connector of a (ejection) needle assembly, when the needle assembly is attached to the dispense interface. The needle assembly may have an injection needle for penetrating the skin of a patient.

As described above, non-limiting examples of a fluid connector may be a piercing needle, a piercable septum and/or a (male/female) Luer-connector. Such a fluid connector may be integrally formed with the body part. Alternatively, such a fluid connector may at least partially be inserted (e.g. potted/over-molded/mounted) into the body part. For instance, such a fluid connector may at least partially be potted/over-molded when the body part is (e.g. injection) molded. For instance, such a fluid connector may at least partially be glued/mounted in a separate step after the body part has been (injection) molded.

The fluid connector forming the at least one outlet of the dispense interface, allows to exchange the needle assembly more often than the dispense interface. This is inter alia advantageous if the needle assembly is a single-use device which has to be replaced after a single ejection and the dispense interface is a disposable part which can be used for more than one ejection.

According to an exemplary embodiment of the dispense interface of the first aspect of the invention, the at least one outlet is formed from a needle, wherein the fluid channel arrangement empties into the needle. The needle may be an injection needle for penetrating the skin of a patient such as a cannula.

The needle may at least partially be inserted (e.g. potted/over-molded/mounted) into the body part. For instance, the needle may at least partially be potted/over-molded when the body part is (e.g. injection) molded. For instance, the needle may at least partially be glued/mounted in a separate step after the body part has been (injection) molded. For instance, the needle may be an integral part of the dispense interface.

Since the at least one outlet is already formed from a needle, no attachment of a separate needle assembly is necessary. This embodiment thus inter-alia allows to reduce the overall complexity of the dispense interface and/or the ejection device. This is inter-alia advantageous if the dispense interface is a single use device which has to be replaced after a single ejection.

According to an exemplary embodiment of the dispense interface of the first aspect of the invention, the dispense interface further comprises an ullage; wherein the tubelike fluid elements provide fluid communication between each of the at least two inlets and the ullage. The tubelike fluid elements may prevent or reduce contact of the guided fluid with the body part at least between each of the at least two inlets and the ullage. The ullage is preferably molded into the body part during molding, in particular injection molding. For instance, the ullage may be a recess, for example a cylindrical or rectangular recess, formed on one side of the body part. Ends of each of the tubelike fluid elements may protrude into the ullage. There may also be provided more than one ullage.

The ullage may also comprise a metal chamber, particularly a steel or stainless steel chamber. The metal chamber may be an insert inserted into the ullage or the metal chamber may be molded into the body part. The metal chamber may at least partially be inserted (e.g. potted/over-molded/mounted) into the body part. For instance, the metal chamber may at least partially be potted/over-molded when the body part is (e.g. injection) molded. For instance, the metal chamber may at least partially be glued/mounted in a separate step after the body part has been (injection) molded. For instance, the metal chamber may be an integral part of the dispense interface.

According to an exemplary embodiment of the dispense interface of the first aspect of the invention, the dispense interface further comprises a valve arrangement, in particular within the ullage, configured to control a fluid flow from the at least two inlets to the at least one outlet via the fluid channel arrangement. The valve arrangement may comprise one or more valves, preferably one or more non-return valves. Such a valve arrangement may preferably be configured to prevent cross contamination of fluids contained in separate fluid reservoirs of the ejection device. A preferred valve arrangement may also be configured so as to prevent back flow. Non-limiting examples of such valves are a diaphragm/flap valve, a shuttling valve, a molded duck bill valve, a flat spring valve and/or a rotating flap valve.

The valve arrangement may for instance be integrally formed with the body part. Alternatively, the valve arrangement may for instance be manufactured separately from the body part. The valve arrangement may be inserted (e.g. potted/over-molded/mounted) into the body part. For instance, the valve arrangement may at least partially be potted/over-molded when the body part is (e.g. injection) molded. For instance, the valve arrangement may at least partially be mounted in a separate step after the body part has been (injection) molded. The valve arrangement may in particular be inserted into the ullage and/or into the metal or molded chamber after molding of the body part. Alternatively, the valve arrangement may be inserted into the ullage of the body part together with the metal chamber.

According to an exemplary embodiment of the dispense interface of the first aspect of the invention, the dispense interface further comprises a film layer; wherein the film layer is bonded to the body part to seal the fluid channel arrangement, in particular the ullage, of the body part. For instance, the film layer may be a metal foil, a polymer film, or a bio-polymer film. The film layer may in particular be a foil or a laminate consisting of two or more layers of different or the same material. For instance, the thickness of the film layer may be 1 μm to 1 mm, in particular 5 μm to 500 μm. For the used materials, a combination of polyamide (PA) and polypropylene (PP) can be used, as PP is biocompatible.

The film layer may be bonded to the body part using adhesive bending techniques or thermal bonding techniques. Non-limiting examples of thermal bonding techniques are laser welding or fusion bonding. The ullage may thus be designed as an accessible recess after molding the body part. After inserting a metal chamber and/or a valve arrangement the ullage may be closed by the film layer sealing the fluid channel arrangement of the body part providing a fluid tight connection between the at least two inlets and the outlet. The film layer may also consist of multiple film layer parts or sections, each bonded to the body part. For the used materials, a combination of polyamide (PA) and polypropylene (PP) can be used, as PP is biocompatible.

For instance, the film layer may be a polymer material, which is biocompatible. For instance, COP (cyclo-olefin polymer) materials may be used for the film layer. COP materials have a high biocompatibility. For instance, COP materials have little to no extractables and most COP materially can undergo sterilization by gamma radiation, steam and/or ethylene oxide. Other materials such as PP (poly-propylene) or HDPE (high density poly-ethylene) or other less expensive materials may be used, too. Especially, the film layer of a single use dispense interface may be made from such a material, as the contact time with the medicament is rather short (only the time from priming the device until the injection is completed). In an example embodiment, the film layer consists of at least 2 layers. The inner layer shall be out of a biocompatible material like cyclo-olefin polymer (COP) or polypropylene (PP), the outer layer can be formed out of material with a higher stiffness like polyamide (PA). By doing so, the foil itself gets a good stiffness and cannot be destroyed easily.

The exemplary embodiments of the dispense interface of the first aspect of the invention allow a simple manufacturing of the dispense interface. Furthermore, they allow manufacturing the body part from a biocompatible material. Potential problems of material compatibility, absorption and cross contamination between the fluids (e.g. drugs) and the polymer material are overcome by the selection of a biocompatible material and/or by providing at least a part of the fluid channel arrangement by the tubelike fluid elements and/or—for a single use dispense interface—by a short contact time.

According to a second aspect of the invention, a method for manufacturing a dispense interface of the first aspect of the invention comprises providing at least two tubelike fluid elements; (e.g. injection) molding each of the tubelike fluid elements into a body part such that each of the tubelike fluid elements provides at least a part of a fluid channel arrangement within the body part.

According to an exemplary embodiment of the method according to the second aspect of the invention, the method further comprises providing a film layer; and bonding the film layer to the body part after molding the body part to seal the fluid channel arrangement of the body part.

According to a third aspect of the invention, a system comprises a dispense interface of the first aspect of the invention; and an ejection device; wherein the dispense interface is attached to the ejection device.

The system may further comprise a needle assembly, wherein the needle assembly is attached to the dispense interface. The dispense interface may provide a fluid connection between at least two separate fluid reservoirs of the ejection device and the needle assembly. As described above, the ejection device may be a medical device configured to deliver (e.g. eject) at least one medicament.

According to a fourth aspect of the invention, a method for using a system of the third aspect of the invention comprises attaching the dispense interface to an ejection device having at least two fluid reservoirs; ejecting a fluid from at least one of the reservoirs through the dispense interface; and detaching the dispense interface from the ejection device.

The method may furthermore comprise attaching a needle assembly to a dispense interface, wherein the fluid is ejected from at least one of the reservoirs through the dispense interface out of the needle assembly.

Exemplary features/embodiments (exhibiting further features) of the invention have been described above, which are understood to apply to the various aspects of the invention. These single features/embodiments are considered to be exemplary and non-limiting, and to be respectively combinable independently from other disclosed features of the various aspects of the invention as described above. Nevertheless, these exemplary features/embodiments shall also be considered to be disclosed in all possible combinations with each other and with the various aspects of the invention as described above.

BRIEF DESCRIPTION OF THE FIGURES

These as well as other advantages of various aspects of the present invention will become apparent to those of ordinary skill in the art by reading the following detailed description, with appropriate reference to the accompanying drawings, in which:

FIG. 12a illustrates a perspective partially transparent view of an alternative embodiment of a dispense interface;

FIGS. 12b-d illustrate alternative embodiments of tubelike fluid elements;

FIG. 13 illustrates the assembly of a rotating flap valve arrangement into the alternative embodiment of the dispense interface illustrated in FIG. 12a;

DETAILED DESCRIPTION

Figure 1:
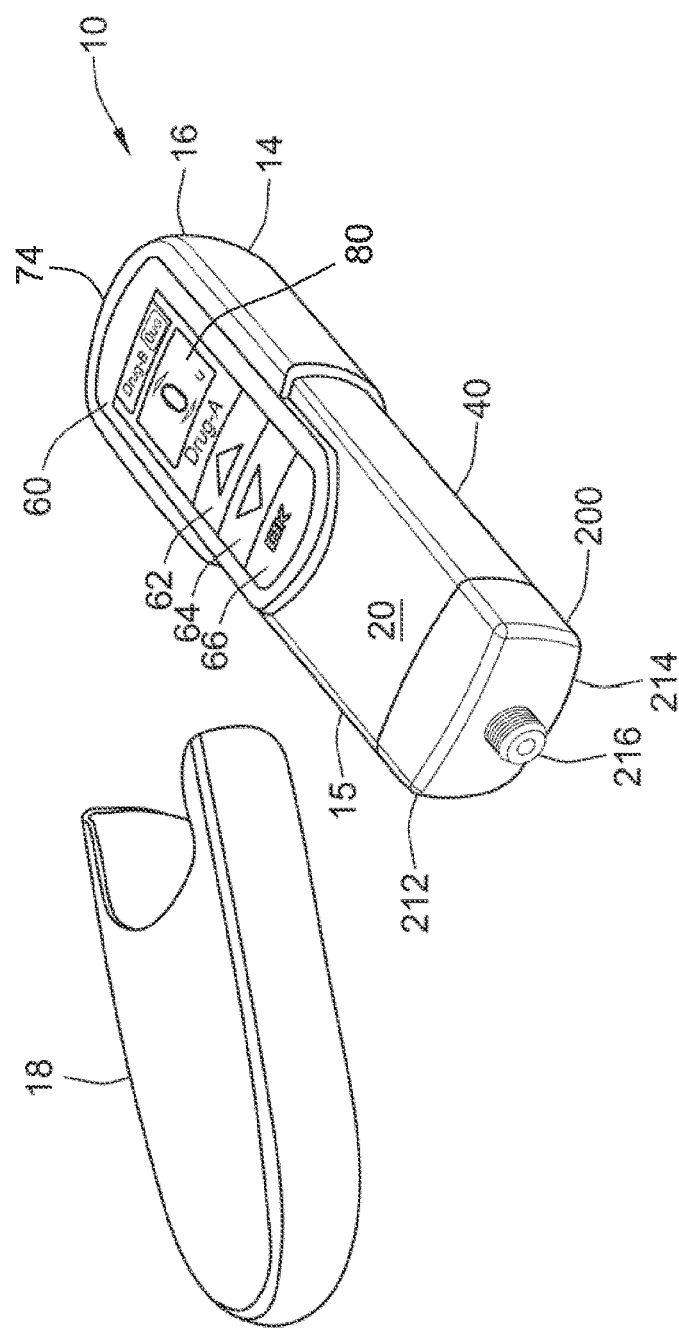
FIG. 1 illustrates a perspective view of a delivery device with an end cap of the device removed.
Figure 2:
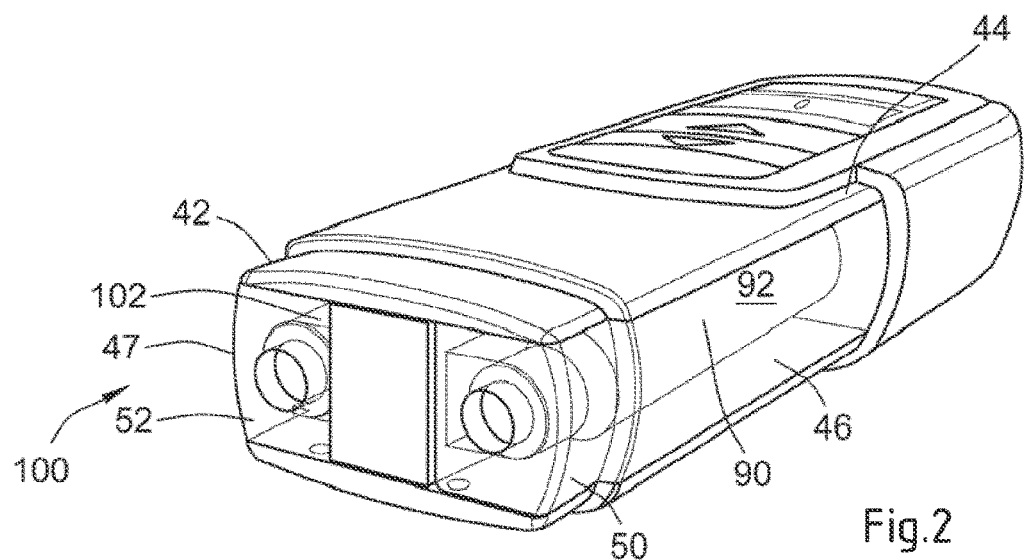
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
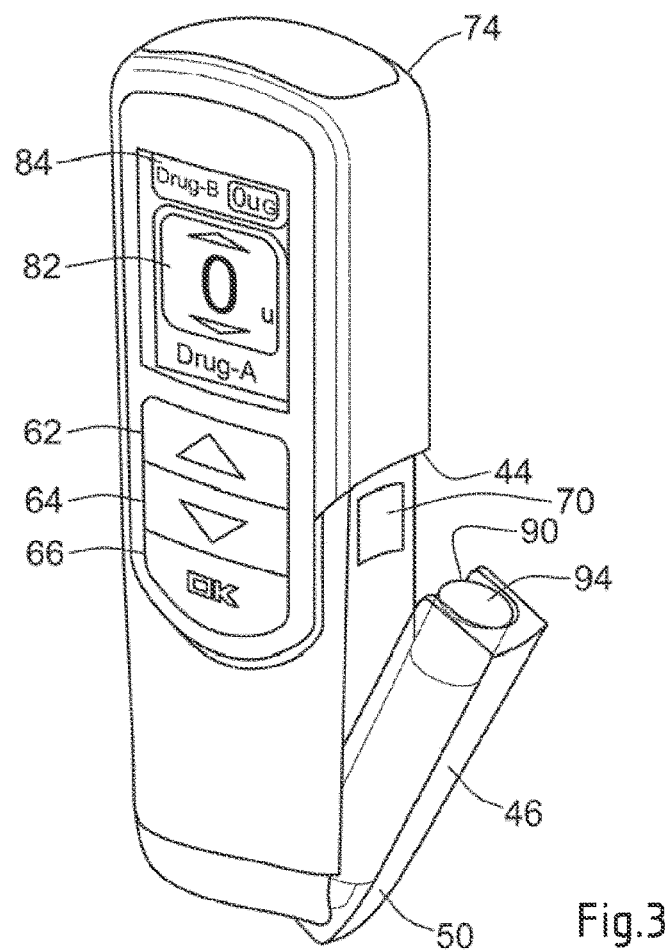
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
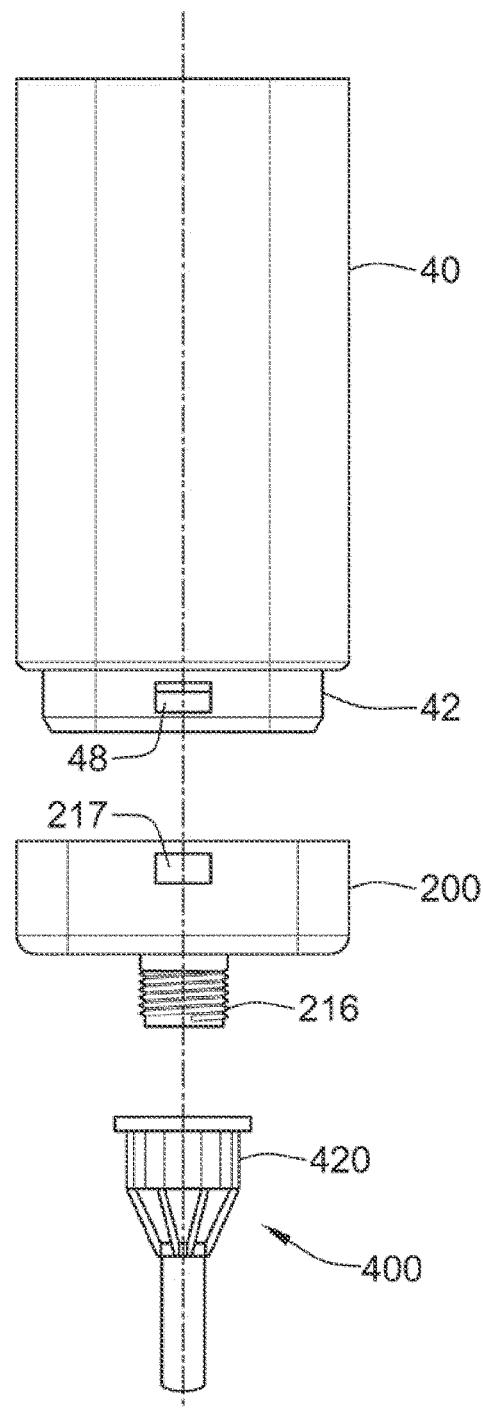
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
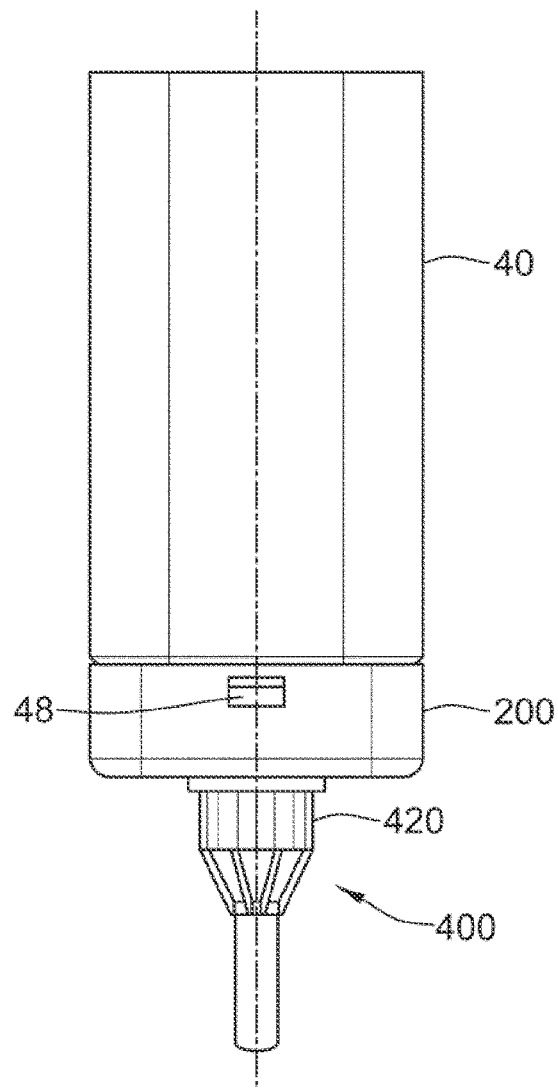
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
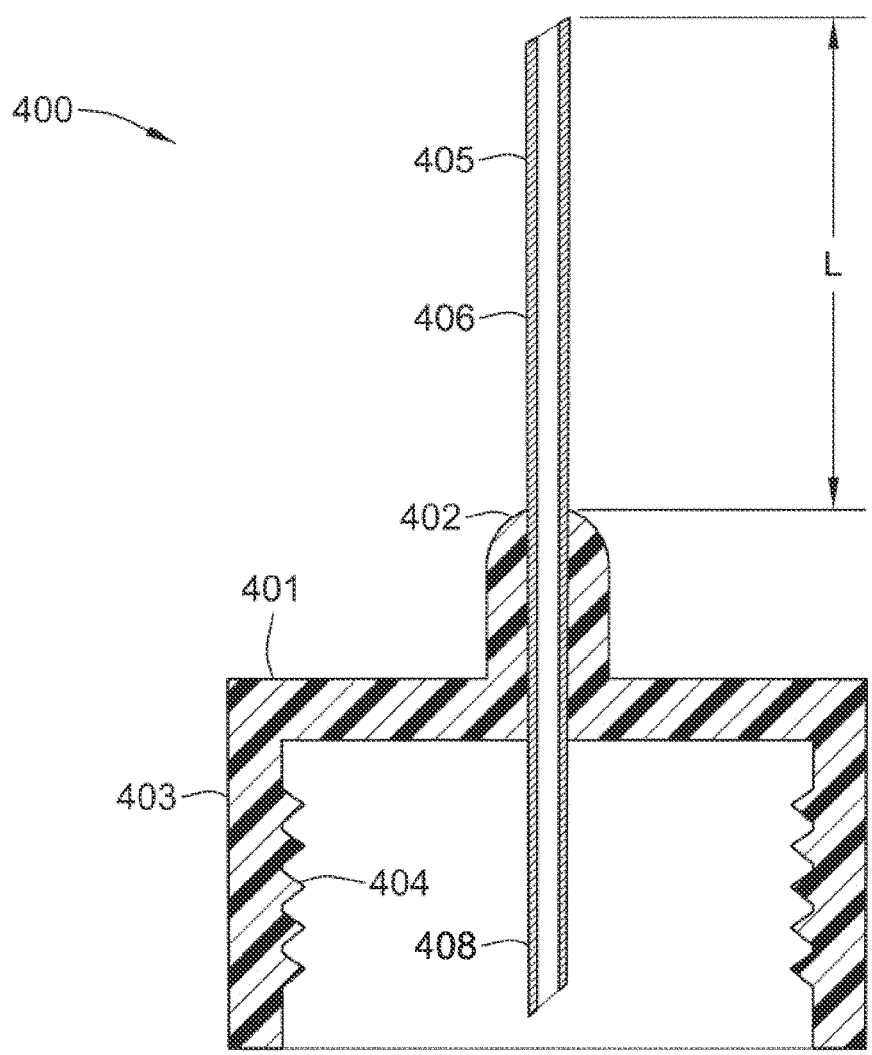
FIG. 6 illustrates one arrangement of a needle assembly that may be mounted on a distal end of the delivery device.
Figure 7:
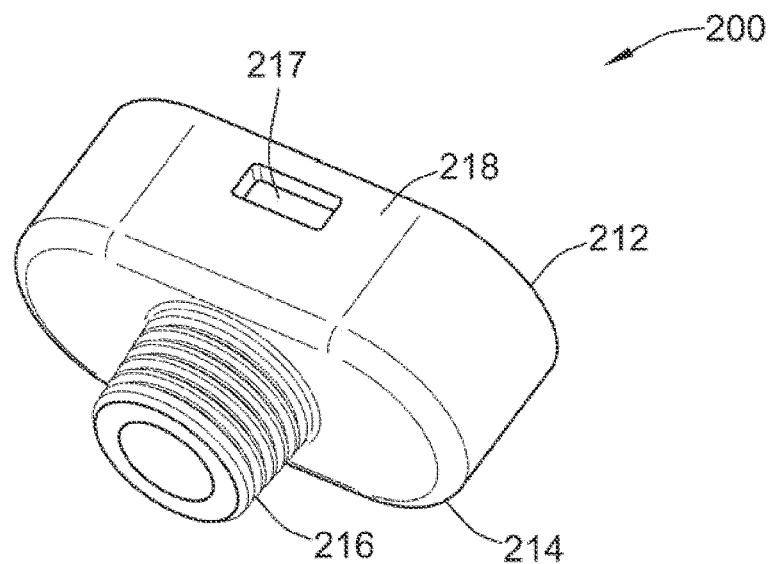
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
   b. an first inner body 220,
   c. a second inner body 230,
   d. a first piercing needle 240,
   e. a second piercing needle 250,
   f. a valve seal 260, and
   g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5.

A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
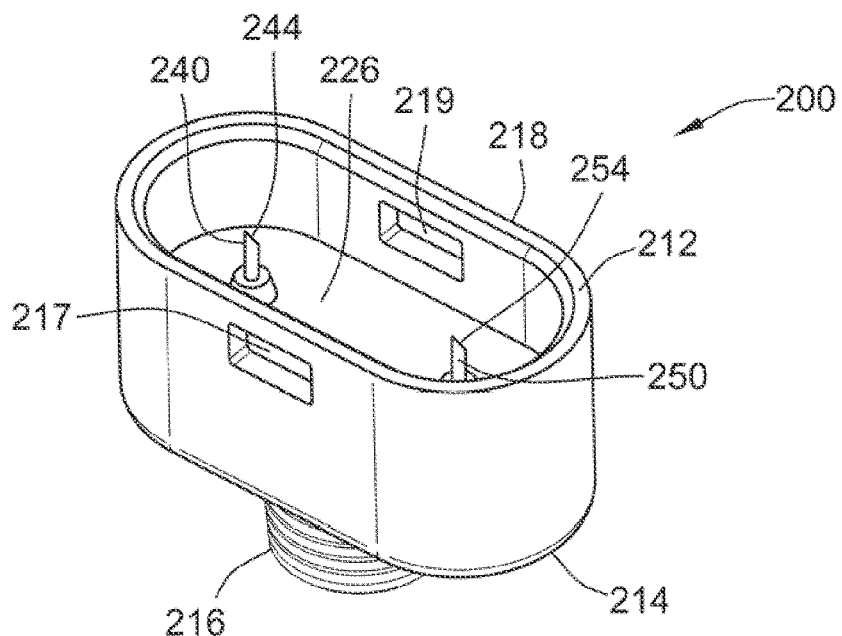
FIG. 8 illustrates another perspective view of the dispense interface illustrated in FIG. 4.
Figure 9:
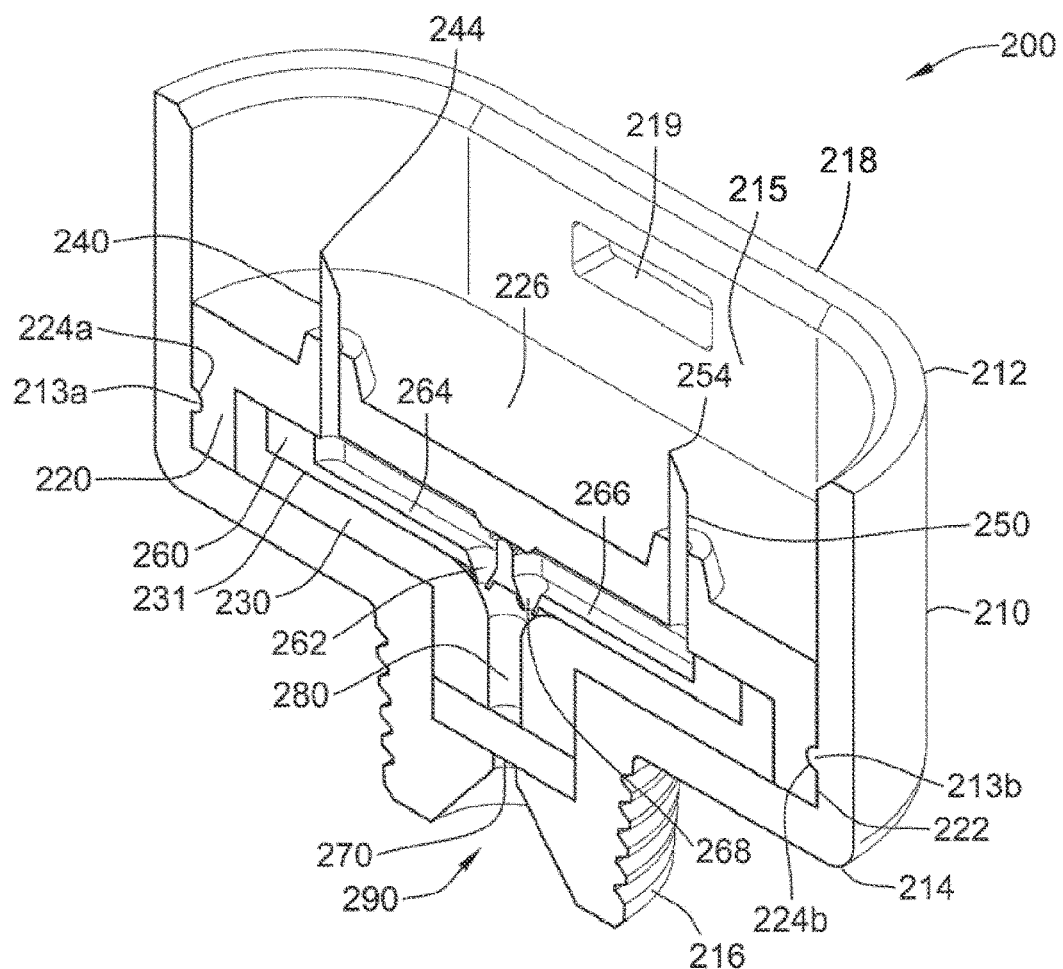
FIG. 9 illustrates a cross-sectional view of the dispense interface illustrated in FIG. 4.
Figure 10:
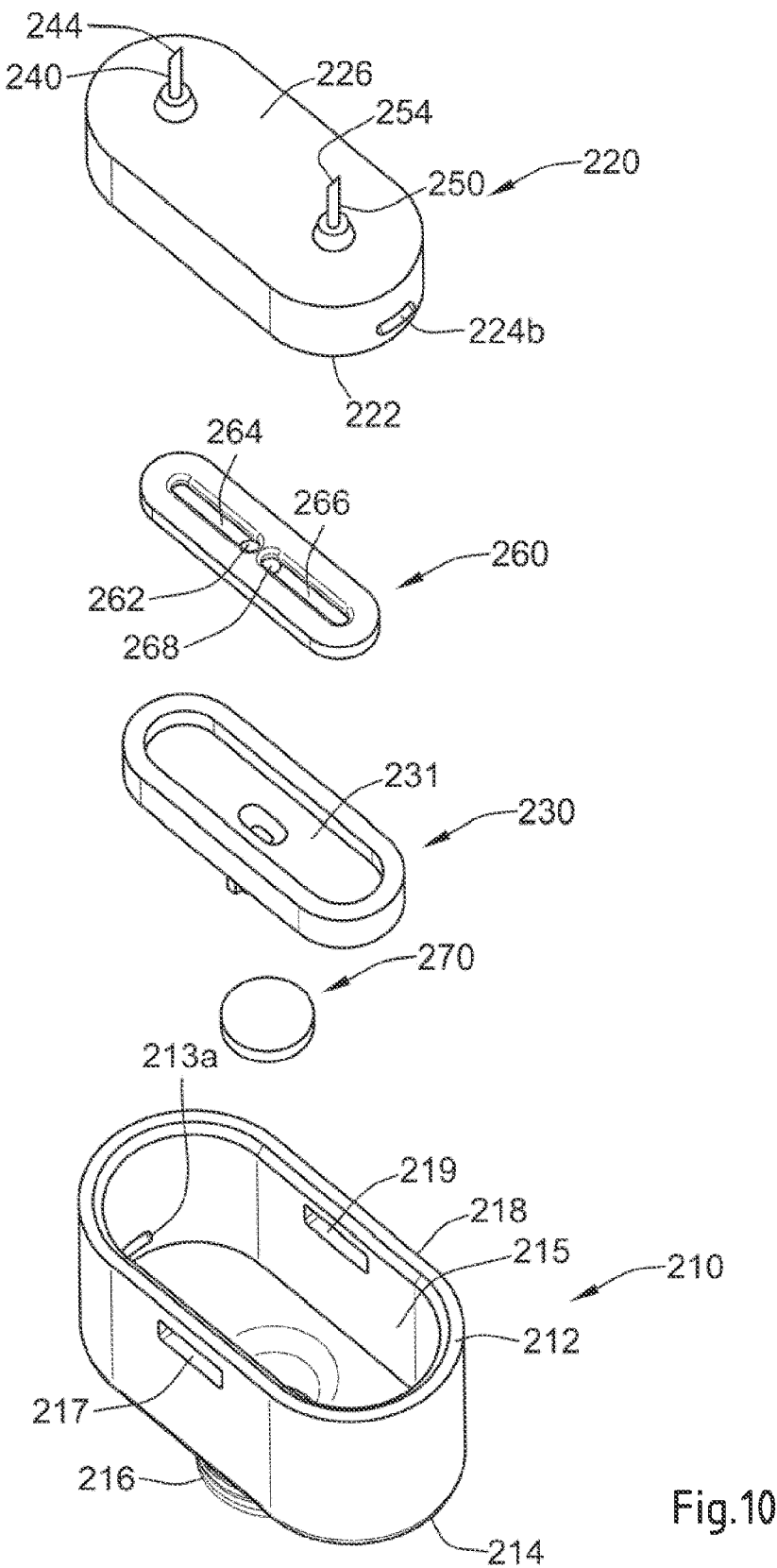
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
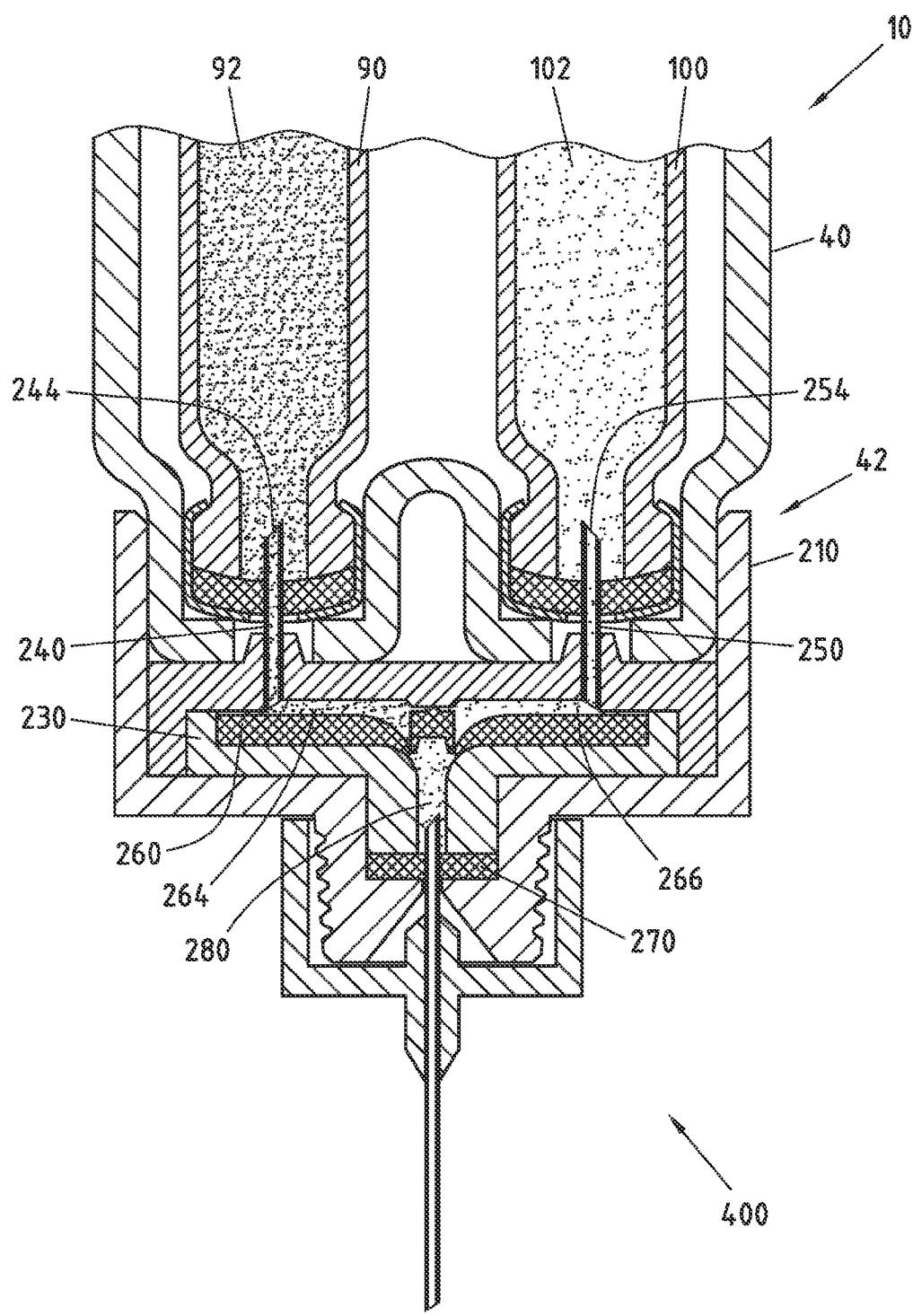
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 13:
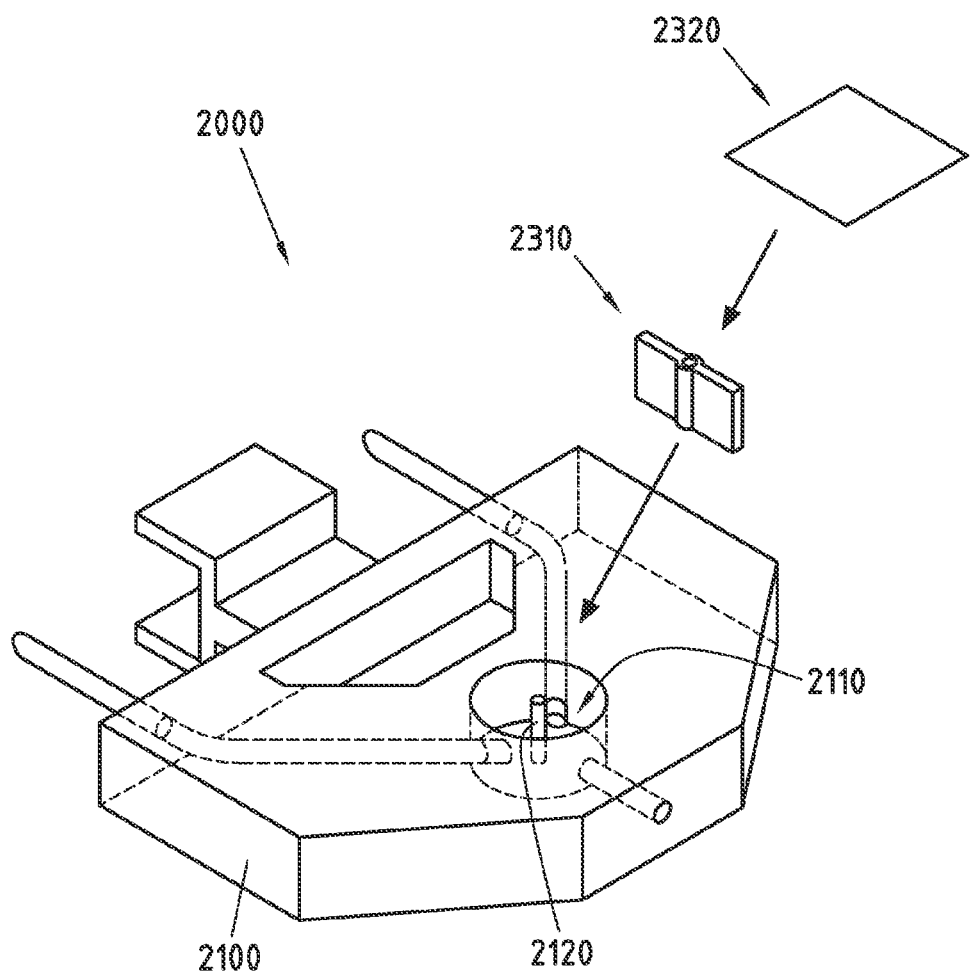

FIGS. 12 to 14 illustrate embodiments of dispense interfaces 2000 alternative to the embodiment of the dispense interface 200 illustrated in FIGS. 7 to 11. Furthermore, at this point, it is mainly referred to the above description of the embodiment of the dispense interface 200 illustrated in FIGS. 7 to 11 and, basically, the differences are described only.

As will now be discussed in greater detail, in one preferred arrangement, the dispense interfaces 2000 illustrated in FIGS. 12 to 14 inter alia comprise:
  a. a body part 2100;
  b. a first tubelike fluid element 2200;
  c. a second tubelike fluid element 2200';
  d. an optional valve arrangement in the form of rotating flap valve arrangement 2300;
  e. an outlet 2400; and
  f. axial attachment means 2500.

One exemplary difference between the dispense interface 200 and the dispense interfaces 2000 is the outer shape. Nevertheless, the dispense interfaces 2000 are attachable to a drug deliver device, for example to the cartridge holder 40 of the drug delivery device 10, by axial attachment means 2500 as described above.

FIG. 12a illustrates a perspective partially transparent view of the alternative embodiment of the dispense interface 2000. The dispense interface 2000 comprises a body part 2100. The body part 2100 is injection molded. The first tubelike fluid element 2200a and the second tubelike fluid element 2200a' are molded into the body part 2100 during the injection molding process. The tubelike fluid elements 2200a, 2200a' are identically designed, but mirror symmetrically fixed in the body part 2100. For instance, the tubelike fluid elements 2200a, 2200a' may also be designed differently from each other.

The tubelike fluid elements 2200a, 2200a' and in particular the protruding ends of the tubelike fluid elements 2200a, 2200a', can thus provide the first and second proximal needles 240, 250 as illustrated in FIGS. 8 to 11.

The first tubelike fluid element 2200a forms a first inlet 2210a of the dispense interface with its first end/opening, while the second tubelike fluid element 2200a forms a second inlet 2210a' of the dispense interface with its first end/opening. The sections of the tubelike fluid elements 2200a, 2200a' protruding from the body part 2100 are substantially linear and protrude substantially perpendicularly from the body part 2100. The tubelike fluid elements 2200a, 2200a' may establish a releasable fluid connection with the fluid reservoirs 90, 100 respectively.

The tubelike fluid elements 2200a, 2200a' are curved or bent inside the body part 2100, as indicated with the dashed lines. The tubelike fluid elements 2200a, 2200a' may deviate from 0° up to 90° (or above) from a linear course, for example. Here, the tubelike fluid elements 2200a, 2200a' deviate about 45° form a linear course (also confer FIG. 12b).

The body part 2100 further comprises a cylindrical ullage 2110. The ullage 2110 is formed as a recess in the surface of the injection molded body part 2100. The second ends 2220a, 2220a' of each of the tubelike fluid elements 2200a, 2200a' protrude from the body part 2100 into the common ullage 2110, providing a fluid connection between the first and second inlets 2210a, 2210a' and the ullage 2110. The ullage further comprises a third fluid pathway being in connection with the fluid outlet 2400. The ullage further comprises a pivot pin 2120, which can be utilized for a rotating flap valve arrangement (also confer FIGS. 13 and 14).

As can be seen from FIG. 12a, a (not yet sealed) fluid channel arrangement is provided within the body part 2100 of the dispense interface 2000 connecting the inlets 2210a, 2210a' with each other and the outlet 2400.

FIG. 12b-c illustrate alternative embodiments of tubelike fluid elements. FIG. 12b exemplarily illustrates the tubelike fluid element 2200a of the tubelike fluid elements 2200a, 2200a' used in the dispense interface 2000 illustrated in FIG. 12a. The tubelike fluid element 2200a is made of a curved or bent needle made of stainless steel. As can be seen, the bent needle 2200a provides a sharp needle tip at its one end forming the first inlet 2210a of the dispense interface 2000. The angle 2230a indicating the deviation of a linear course of the tubelike fluid element 2200a is about 45°. However, smaller or larger curvatures and/or smaller or larger angles may be provided.

FIG. 12c illustrates an alternative tubelike fluid element in the form of a hypo-tube 2200b in a linear state, which may be used instead of the tubelike fluid elements 2200a, 2200a' in form of bent needles. The hypo-tube 2200b may also be manufactured from stainless steel. The hypo-tube 2200b has a middle section 2240b, which section may be laser cut, for example helically, increasing the mechanical flexibility of the hypo-tube in the section 2240b. A polymer sheath is also provided in the section 2240b on the outside of the hypo-tube to ensure fluid tightness. The hypo-tube 2200b can be flexibly bent, for example in an S-like shape, as illustrated in FIG. 12d.

FIG. 13 illustrates the assembly of a rotating flap valve arrangement 2300 into the alternative embodiment of the dispense interface illustrated in FIG. 12a. The rotating flap valve arrangement 2300 has a flap 2310 which is rotatably mounted on the pivot pin 2120 of the ullage 2110.

The flap 2310 is rotatable between a first and a second position. The working principle of the rotatable flap valve arrangement, however, is described in more details below with respect to FIGS. 14b and 15e.

After the rotatable flap 2310 is inserted in the ullage 2110, a film layer 2320 is used in order to seal the ullage of the body part 2100 by bonding the film layer to said body part 2100. A fluid tight connection is thus achieved between the first inlet 2210a and the outlet 2400 and between the second inlet 2210a' and the outlet 2400.

Figure 14A:
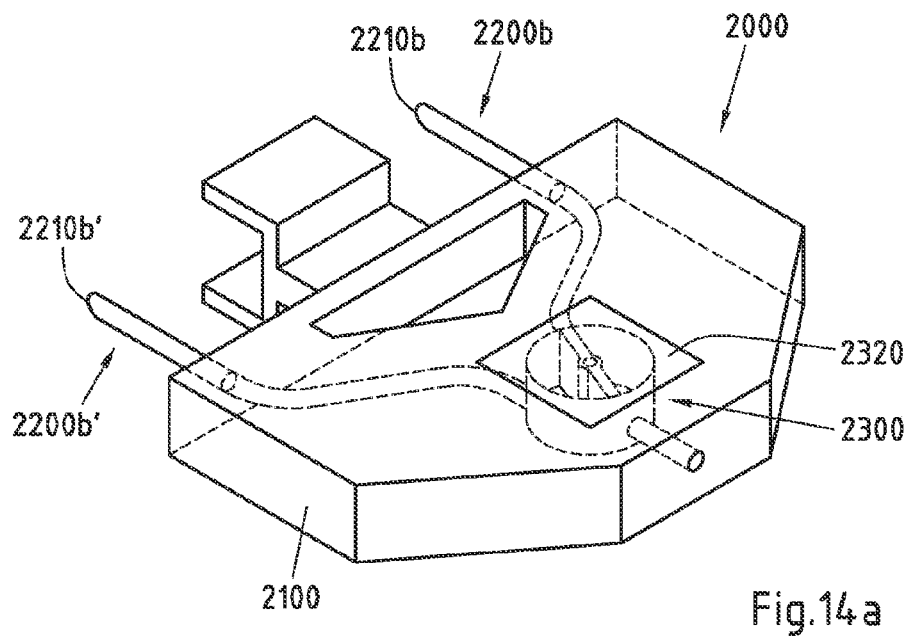
FIGS. 14a-b illustrate a further alternative embodiment of a dispense interface similar to the one illustrated in FIG. 12a after the assembly steps illustrated in FIG. 13.

FIG. 14a illustrates a further alternative embodiment of a dispense interface 2000 similar to the dispense interface 2000 illustrated in FIG. 12a after the assembly steps illustrated in FIG. 13. In FIG. 14a the same reference signs as in FIG. 12a are used for parts which are similar.

The only difference of the dispense interface 2000 from FIG. 14a compared to the one from FIG. 12a is that instead of the tubelike fluid elements 2200a, 2200a' illustrated in FIG. 12b in the form of bent needles the tubelike fluid elements 2200b, 2200b' illustrated in FIG. 12d in the form of hypo-tubes are molded into the body part 2100.

Figure 14B:
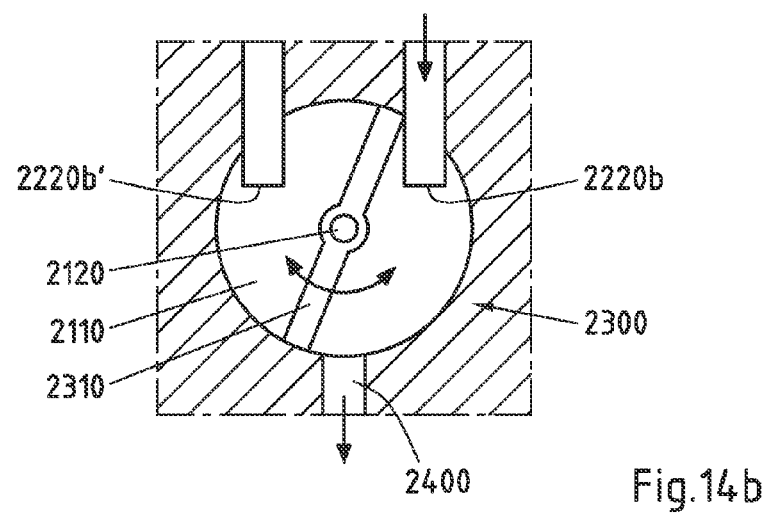

FIG. 14b shows an enlarged view of the rotating flap valve arrangement 2300. The flap 2310 of the rotating flap valve arrangement 2300 mounted in the ullage 2110 can rotate about the pivot pin 2120. The ullage 2110 providing a valve chamber has two inlets provided by the ends 2220b, 2220b' of the tubelike fluid elements 2200b and 2220b' and a third fluid pathway being in connection with the outlet 2400 of the dispense interface 2000.

The flap 2310 is rotatable between a first and a second position. In the first position (illustrated in FIG. 14b), the flap 2310 seals the inlet 2220b' and allows fluid to flow from the inlet 2220b to the outlet 2400. In the second position (not illustrated), the flap 2310 seals the inlet 2220b and allows fluid to flow from the inlet 2220b' to the outlet 2400.

When the fluidic pressure in the inlet 2220b' is for instance increased (e.g. during a dose priming or a dose injecting step), the flap 2310 will be pushed towards the second position as indicated by the arrow in FIG. 14b and vice versa.

However, the dispense interfaces 2000 may also comprise no valve arrangement or any alternative valve arrangement such as one of the embodiments illustrated in FIGS. 15a to 15e.

The function of the rotating flap valve arrangement 2300 of the dispense interfaces 2000 may basically relate to the function of the first and second non return valve 262, 264 of the dispense interface 200. As described above, such a valve arrangement may for instance be constructed so as to prevent back flow and/or cross contamination of the first and second medicaments 92, 102 contained in the first and second reservoirs 90, 100, respectively.

FIGS. 15a to 15e illustrate embodiments of a valve arrangement for a dispense interface alternative to the valve seal 260 of dispense interface 200 and rotating flap valve 2300 of dispense interface 2000, respectively. In FIGS. 15a to 15e the same reference signs are used for parts which are similar.

The valve arrangement may for instance be integrally formed with another part of the dispense interface. Alternatively, the valve arrangement may for instance be manufactured separately from the other parts of dispense interface.

For instance, the valve arrangement may be inserted (e.g. potted/over-molded/mounted) into the body part. For instance, the valve arrangement may at least partially be potted/over-molded when body part is (e.g. injection) molded. For instance, the valve arrangement may at least partially be mounted in a separate step after the body part has have been (injection) molded.

Figure 15A:
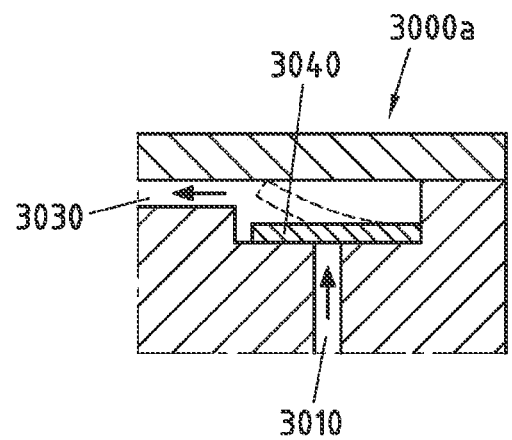
FIG. 15a illustrates an alternative embodiment of a valve arrangement of a dispense interface.

FIG. 15a illustrates a diaphragm/flap valve arrangement 3000a. The diaphragm/flap valve arrangement 3000a has an inlet 3010 and an outlet 3030. The inlet 3010 may for instance reside in fluid communication with one of the piercing needles 240, 250 of dispense interface 200 or 2000 and the outlet 3030 may for instance reside in fluid communication with holding chamber 280 of dispense interface 200 or the outlet 2400 of dispense interface 2000.

The diaphragm/flap valve arrangement 3000a has a flexible diaphragm/flap 3040. When the fluidic pressure in the inlet 3010 is increased (e.g. during a dose priming or a dose injecting step), the diaphragm/flap 3040 will change from an un-stressed state to a stressed state. In the stressed state, the fluidic pressure bends the diaphragm/flap 3040 as indicated by the arrow in FIG. 15a so that the diaphragm/flap valve arrangement 3000a opens. In this stressed condition, the diaphragm/flap valve arrangement 3000a will allow fluid to flow from the inlet 3010 to the outlet 3030. When the fluidic pressure in the inlet is removed, the diaphragm/flap 3040 will return to its initial position and seal the inlet 3010, preventing backflow.

Figure 15B:
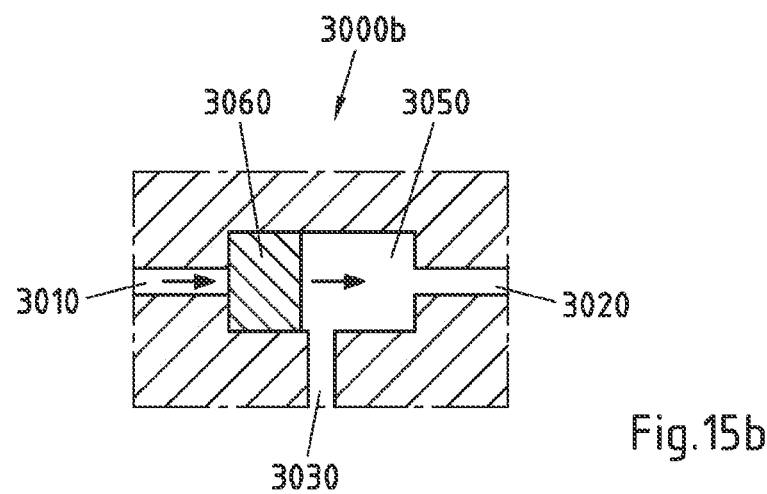
FIG. 15b illustrates another alternative embodiment of a valve arrangement of a dispense interface.

FIG. 15b illustrates a shuttling valve arrangement 3000b. The shuttling valve arrangement 3000b has a tube 3050. The tube 3050 has two inlets 3010, 3020 and an outlet 3030. The inlet 3020 may also reside in fluid communication with one of the piercing needles 240, 250 of dispense interface 200 or 2000. In the tube 3050 a movable element 3060 (e.g. a piston or a ball) is arranged.

The diameter of the movable element 3060 corresponds to the diameter of the tube 3050 such that the movable element 3060 is movable between a first and a second (longitudinal) position in the tube 3050. In the first position (illustrated in FIG. 15b), the movable element 3060 seals the inlet 3010 and allows fluid to flow from the inlet 3020 to the outlet 3030. In the second position (not illustrated), the movable element 3060 seals the inlet 3020 and allows fluid to flow from the inlet 3010 to the outlet 3030. When the fluidic pressure in the inlet 3010 is for instance increased (e.g. during a dose priming or a dose injecting step), the movable element 3060 will be pushed towards the second position as indicated by the arrow in FIG. 15b.

Figure 15C:
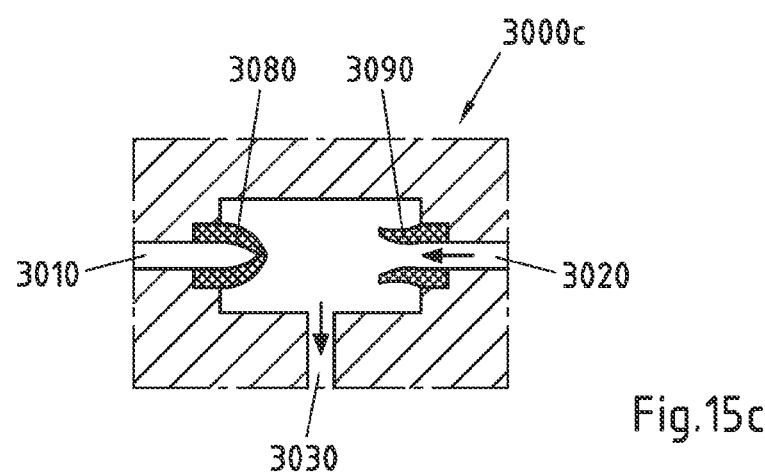
FIG. 15c illustrates another alternative embodiment of a valve arrangement of a dispense interface.

FIG. 15c illustrates a molded duckbill valve arrangement 3000c. The molded duckbill valve arrangement 3000c has a first and a second duckbill valve 3080, 3090. When the fluidic pressure in the inlet 3020 is increased (e.g. during a dose priming or a dose injecting step), the second duckbill valve 3090 will change from an un-stressed state to a stressed state. In the stressed state, the fluidic pressure inverts the naturally flattened shape of the duckbill valve as indicated in FIG. 15c so that the duckbill valve opens. In this stressed condition, the second duckbill valve 3090 will allow fluid to flow from the inlet 3020 to the outlet 3030.

When the fluidic pressure in the inlet 3020 is removed, the second duckbill valve 3090 will return to its flattened shape and seal the inlet 3020, preventing backflow. The first duckbill valve 3080 operates in a similar manner as the second duckbill valve 3090 when the fluidic pressure is increased in the inlet 3010.

Figure 15D:
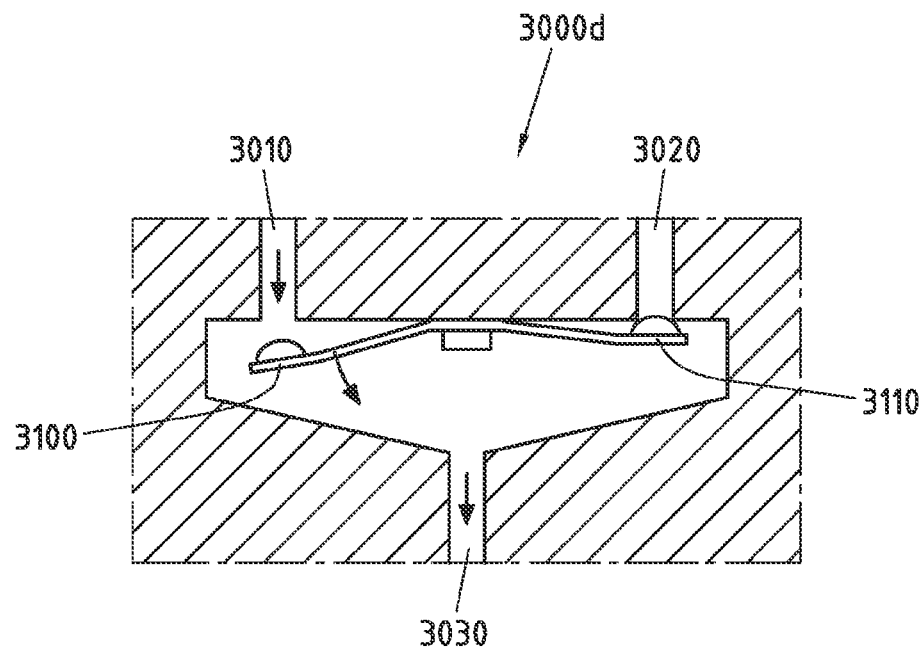
FIG. 15d illustrates another alternative embodiment of a valve arrangement of a dispense interface.

FIG. 15d illustrates a flat spring valve arrangement 3000d. The flat spring valve arrangement 3000d has a first and a second flat spring 3100, 3110. The first and the second flat spring 3100, 3110 may for instance be integrally formed.

When the fluidic pressure in the inlet 3010 is increased (e.g. during a dose priming or a dose injecting step), the first flat spring 3100 will change from an un-stressed state to a stressed state. In the stressed state, the fluidic pressure bends the first flat spring 3100 as indicated by the arrow in FIG. 15d so that the flat spring valve arrangement 3000d opens. In this stressed condition, the flat spring valve arrangement 3000d will allow fluid to flow from the inlet 3010 to the outlet 3030. When the fluidic pressure in the inlet 3010 is removed, the first flat spring 3100 will return to its initial position and seal the inlet 3010, preventing backflow. The second flat spring 3110 operates in a similar manner as the first flat spring 3100 when the fluidic pressure is increased in the inlet 3020.

Figure 15E:
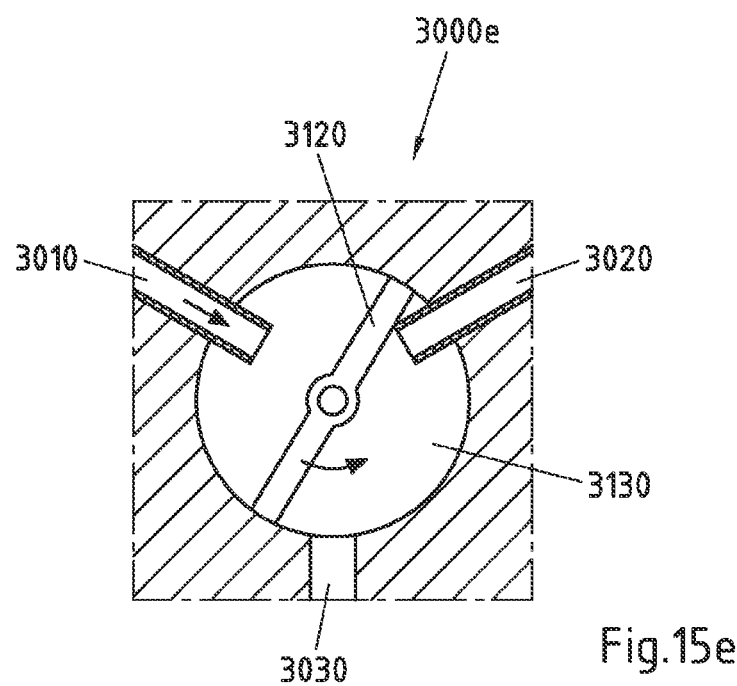
FIG. 15e illustrates another alternative embodiment of a valve arrangement of a dispense interface.

FIG. 15e illustrates a rotating flap valve arrangement 3000e. The rotating flap valve arrangement 3000e has a flap 3120 which is rotatably mounted in a valve chamber 3130. The valve chamber has two inlets 3010, 3020 and an outlet 3030.

The flap 3120 is rotatable between a first and a second position. In the first position (illustrated in FIG. 15e), the flap 3120 seals the inlet 3010 and allows fluid to flow from the inlet 3020 to the outlet 3030. In the second position (not illustrated), the flap 3120 seals the inlet 3020 and allows fluid to flow from the inlet 3010 to the outlet 3030.

When the fluidic pressure in the inlet 3010 is for instance increased (e.g. during a dose priming or a dose injecting step), the flap 3120 will be pushed towards the second position as indicated by the arrow in FIG. 15e.

Figure 16:
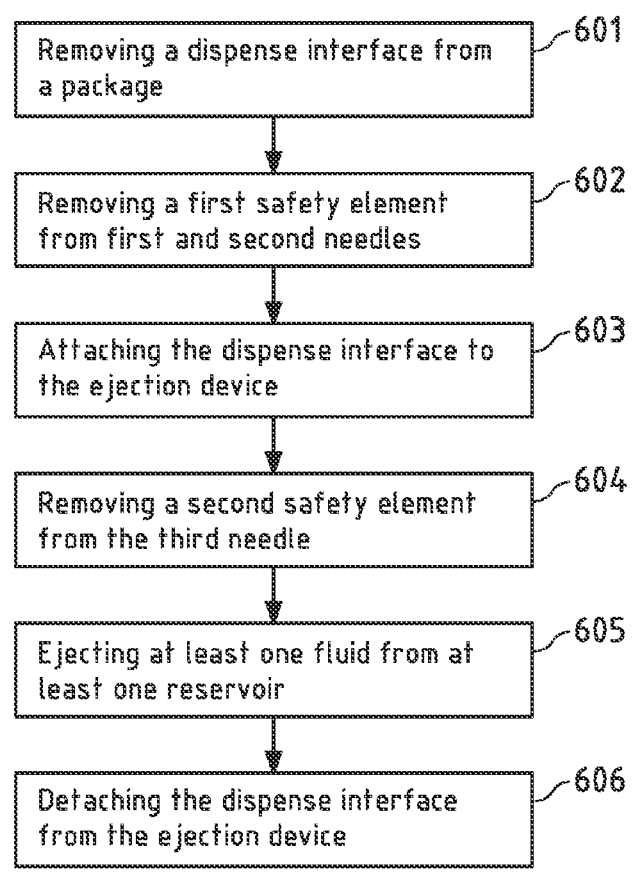
FIG. 16 illustrates a flowchart of a method according to the invention for using a dispense interface.

FIG. 16 illustrates a flowchart of a method according to the invention for using a dispense interface. In particular, the use of a previously described dispense interface is illustrated.

In a first step 601, a packaging of the dispense interface can be opened by a user and the dispense interface can be taken from the packaging.

Then, in step 602, if the dispense interface is provided with a first safety element, like a needle cover, the first safety element can be removed from the first proximal needle and/or the second proximal needle, each of which may be provided by a tubelike fluid element. For instance, if a predetermined braking line is provided, the first safety element can be detached by an angular movement performed by the user. It shall be understood that in alternative embodiments, the safety element can be formed by caps or the like.

After removing the first safety element, the first and second proximal needles are exposed. Then in step 603, the dispense interface is attached to an ejection device. In particular, the dispense interface is tightly attached to the ejection device. Thereby, the first proximal needle can puncture a first reservoir and the second proximal needle can puncture a second reservoir of the ejection device.

If the dispense interface comprises a second safety element for covering an ejection needle, which is in fluid communication with the outlet 2400, in step 604, the second safety element is removed. The third needle, like an ejection needle, is exposed. For instance, if a predetermined breaking line is provided, the safety element can be removed by a circular and pull movement performed by the user. For avoiding a detachment of the dispense interface from the ejection device, the predetermined breaking line can be first cut by the circular movement and then the safety element can be removed by a pull movement.

In the next step 605, at least one fluid of at least one reservoir can be ejected, as described hereinbefore. For instance, a drug or medicament can be ejected.

Afterwards, the used dispense interface is detached from the ejection device (step 606). For instance, the used dispense interface can be pulled out by the user.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for an ejection device, said dispense interface comprising:
    at least two inlets;
    at least one outlet;
    an integral body part; and
    a fluid channel arrangement within said integral body part configured to provide fluid communication between said at least two inlets and said at least one outlet;
    an ullage formed as a recess in a surface of the integral body part;
    a rotatable flap positioned within the ullage, wherein the rotatable flap is rotatably coupled to the ullage, and wherein the rotatable flap is configured to control a fluid flow from said at least two inlets to said at least one outlet via said fluid channel arrangement;
    wherein each of said at least two inlets is formed from a tubelike fluid element, wherein the tubelike fluid elements provide fluid communication between each of the at least two inlets and the ullage;
    wherein each of said tubelike fluid elements is molded into the integral body part; and
    wherein each of said tubelike fluid elements provides at least a part of the fluid channel arrangement within said integral body part and
    wherein each of said tubelike fluid elements has a fluid pathway that is at least partially curved.

2. The dispense interface according to claim 1, wherein each of said tubelike fluid elements is configured to establish a releasable fluid connection with a corresponding fluid connector of a fluid reservoir of said ejection device when said dispense interface is attached to said ejection device.

3. The dispense interface according to claim 1, wherein each of said tubelike fluid elements is a needle or a hypotube.

4. The dispense interface according to claim 1, wherein said at least one outlet is formed from a fluid connector, wherein said fluid channel arrangement empties into said fluid connector, and wherein said fluid connector is configured to establish a fluid connection with a corresponding fluid connector of a needle assembly, when said needle assembly is attached to said dispense interface.

5. The dispense interface according to claim 1, wherein said at least one outlet is formed from a needle, wherein said fluid channel arrangement empties into said needle.

6. The dispense interface according to claim 1, said dispense interface further comprising:
    a film layer;
    wherein said film layer is bonded to said integral body part to seal said ullage of said integral body part.

7. A method for manufacturing a dispense interface according to claim 1, said method comprising:
    providing at least two tubelike fluid elements; wherein each of said tubelike fluid elements has a fluid pathway that is at least partially curved; and
    molding each of said tubelike fluid elements into an integral body part such that each of said tubelike fluid elements provides at least a part of a fluid channel arrangement within said integral body part.

8. A method according to claim 7, said method further comprising:
    providing a film layer; and
    bonding said film layer to said integral body part after molding the integral body part to seal said fluid channel arrangement of said body part.

9. A system, comprising
    a dispense interface according to claim 1;
    an ejection device;
    wherein said dispense interface is attached to said ejection device.

10. The system according to claim 9, said system further comprising:
    a needle assembly;
    wherein said needle assembly is attached to said dispense interface.

11. The system according to claim 9, wherein said ejection device is a medical device configured to eject a medicament.

12. The method for using a system according to claim 9, said method comprising:
- attaching said dispense interface to an ejection device having at least two fluid reservoirs;
- ejecting a fluid from at least one of the reservoirs through said dispense interface; and
- detaching said dispense interface from said ejection device.

* * * * *